(12) United States Patent
Fuimaono et al.

(10) Patent No.: US 7,228,164 B2
(45) Date of Patent: *Jun. 5, 2007

(54) CATHETER AND METHOD FOR MAPPING PURKINJE FIBERS

(75) Inventors: Kristine B. Fuimaono, Covina, CA (US); Bart-Jan Korteling, Leek (NL); Michel Haissaguerre, Talence (FR)

(73) Assignee: Biosense Webster Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/025,448

(22) Filed: Dec. 29, 2004

(65) Prior Publication Data

US 2005/0113660 A1 May 26, 2005

Related U.S. Application Data

(62) Division of application No. 10/231,857, filed on Aug. 30, 2002, now Pat. No. 7,089,045.

(51) Int. Cl.
*A61B 5/0402* (2006.01)

(52) U.S. Cl. .................. 600/374; 128/899; 607/122

(58) Field of Classification Search ............... 600/374; 606/41; 607/122; 128/898
See application file for complete search history.

(56) References Cited

U.S. PATENT DOCUMENTS

| | | | |
|---|---|---|---|
| 3,769,984 | A | 11/1973 | Muench |
| 3,995,623 | A | 12/1976 | Blake et al. |
| 4,444,195 | A | 4/1984 | Gold |
| 4,522,212 | A | 6/1985 | Gelinas et al. |

(Continued)

FOREIGN PATENT DOCUMENTS

DE 19915689 A1 10/1999

(Continued)

OTHER PUBLICATIONS

International Search Report for European Application No. 03255303.4 filed Aug. 27, 2003.

*Primary Examiner*—Lee S. Cohen
(74) *Attorney, Agent, or Firm*—Christie, Parker & Hale, LLP.

(57) ABSTRACT

An improved catheter is provided that is particularly useful for mapping the Purkinje fibers for potential diagnosis of ventricular fibrillation. The catheter comprises an elongated catheter body having proximal and distal ends and at least one lumen extending longitudinally therethrough. Mounted at the distal end of the catheter body is a mapping assembly having at least two spines, each having a proximal end attached at the distal end of the catheter body and a free distal end. Each spine comprises at least one electrode, preferably a tip electrode and at least one ring electrode. An irrigation tube extends through the catheter body and has an open distal end that is in communication with the outside of the distal end of the catheter body. The spines may be arranged in an expanded arrangement wherein each spine extends radially outwardly from the catheter body or in a collapsed arrangement wherein each spine is disposed generally along the longitudinal axis of the catheter body. In use, at least one electrode from each spine is positioned in contact with heart tissue to map the electrical activity of the heart. The location sensors are used to determine the location of each point where the electrical activity is monitored.

7 Claims, 7 Drawing Sheets

U.S. PATENT DOCUMENTS

| | | | |
|---|---|---|---|
| 4,592,372 A | 6/1986 | Beranek | |
| 4,777,955 A | 10/1988 | Brayton et al. | |
| 5,237,996 A | 8/1993 | Waldman et al. | |
| 5,282,845 A | 2/1994 | Bush et al. | |
| 5,327,889 A | 7/1994 | Imran | |
| 5,391,199 A | 2/1995 | Ben-Haim | |
| 5,411,025 A | 5/1995 | Webster, Jr. | |
| 5,433,198 A | 7/1995 | Desai | |
| 5,551,426 A * | 9/1996 | Hummel et al. | 600/374 |
| 5,567,901 A | 10/1996 | Gibson et al. | |
| 5,628,313 A | 5/1997 | Webster, Jr. | |
| 5,683,384 A | 11/1997 | Gough et al. | |
| 5,702,438 A | 12/1997 | Avitall | |
| 5,728,143 A | 3/1998 | Gough et al. | |
| 5,741,214 A | 4/1998 | Ouchi et al. | |
| 5,772,590 A | 6/1998 | Webster, Jr. | |
| 5,782,239 A | 7/1998 | Webster, Jr. | |
| 5,855,552 A | 1/1999 | Houser et al. | |
| 5,855,576 A | 1/1999 | LeVeen et al. | |
| 5,908,446 A | 6/1999 | Imran | |
| 5,935,102 A | 8/1999 | Bowden et al. | |
| 5,938,694 A | 8/1999 | Jaraczewski et al. | |
| 5,951,547 A | 9/1999 | Gough et al. | |
| 6,068,629 A | 5/2000 | Haissaguerre et al. | |
| 6,071,280 A | 6/2000 | Edwards et al. | |
| 6,144,870 A | 11/2000 | Griffin, III | |
| 6,163,716 A * | 12/2000 | Edwards et al. | 600/374 |
| 6,206,874 B1 | 3/2001 | Ubby et al. | |
| 6,216,044 B1 | 4/2001 | Kordis | |
| 6,221,107 B1 | 4/2001 | Steiner | |
| 6,231,570 B1 | 5/2001 | Tu et al. | |
| 6,237,605 B1 | 5/2001 | Vaska et al. | |
| 6,266,552 B1 | 7/2001 | Slettenmark | |
| 6,285,898 B1 | 9/2001 | Ben-Haim | |
| 6,374,476 B1 | 4/2002 | Ponzi et al. | |
| 6,389,311 B1 | 5/2002 | Whayne et al. | |
| 6,402,746 B1 | 6/2002 | Whayne et al. | |
| 6,551,311 B2 | 4/2003 | Lee et al. | |
| 6,574,492 B1 * | 6/2003 | Ben-Haim et al. | 600/374 |
| 6,638,277 B2 | 10/2003 | Schaefer et al. | |
| 2001/0001819 A1 | 5/2001 | Lee et al. | |
| 2002/0026188 A1 | 2/2002 | Balbierz et al. | |
| 2002/0068867 A1 | 6/2002 | Ameling et al. | |
| 2002/0087157 A1 | 7/2002 | Sliwa, Jr. et al. | |
| 2003/0050637 A1 | 3/2003 | Maguire et al. | |
| 2003/0125614 A1 * | 7/2003 | Fuimaono et al. | 600/374 |

FOREIGN PATENT DOCUMENTS

| | | |
|---|---|---|
| EP | 1120082 A1 | 8/2001 |
| WO | WO 96/05768 | 2/1996 |
| WO | WO 97/24981 | 7/1997 |
| WO | WO 97/24983 | 7/1997 |

* cited by examiner

CATHETER AND METHOD FOR MAPPING PURKINJE FIBERS

CROSS-REFERENCE TO RELATED APPLICATION(S)

This application is a divisional of application Ser. No. 10/231,857, filed Aug. 30, 2002, now U.S. Pat. No. 7,089,045, entitled CATHETER AND METHOD FOR MAPPING PURKINJE FIBERS.

BACKGROUND OF THE INVENTION

Ventricular fibrillation is the main mechanism of sudden cardiac death. Recent studies revealed that premature beats originate from the Purkinje fibers, a specialized intraventricular conducting system. The premature beats were found to originate from both the left and right ventricles. These premature beats are the dominant sources of iodiopathic ventricular fibrillation and accompanying close coupled ventricular ectopic beats. These sources can be eliminated by local energy delivery, for example, by ablation using radio frequency energy. It would be desirable to provide a device that could easily and efficiently map the Purkinje fibers to permit effective targeted radio frequency delivery to eliminate premature beats and local Purkinje potentials.

SUMMARY OF THE INVENTION

The present invention is directed to an improved catheter for mapping the electrical activity in a heart that is particularly useful for mapping the Purkinje fibers for potential diagnosis of ventricular fibrillation. The catheter comprises a plurality of spines each capable of obtaining electrical, mechanical and/or locational data. The use of a plurality of spines permits simultaneous mapping of multiple points, increasing the speed of mapping of regions of interest, e.g., the left and right ventricles. The spines are designed to permit all of the spines to simultaneously contact the heart tissue in and around the uniquely-shaped chambers of the left and right ventricles.

In one embodiment, the invention is directed to a catheter comprising an elongated catheter body having a proximal end, a distal end and at least one lumen extending longitudinally therethrough. A mapping assembly is mounted at the distal end of the catheter body and comprises at least two spines. Each spine has a proximal end attached at the distal end of the catheter body and a free distal end, and each spine comprises at least one electrode, and preferably at least one location sensor. An irrigation tube extends through the catheter body and has an open distal end that is in communication with the outside of the distal end of the catheter body.

In another embodiment the invention is directed to a method for mapping Purkinje fibers. The method comprises introducing the distal end of a catheter as described above into a region of the heart around or near a ventricle. The mapping assembly is positioned so that at least one electrode from each spine is in contact with a first plurality of heart tissue. Electrical data from the first plurality of heart tissue is recorded. The mapping assembly is repositioned such that at least one electrode from each spine contacts a second different plurality of heart tissue. Electrical data from the second plurality of heart tissue is then recorded.

In another embodiment the invention is directed to a method for mapping a region of the heart. The method comprises introducing the distal end of a catheter as described above into a region of the heart around or near a ventricle. The mapping assembly is positioned so that at least one electrode from each spine is in contact with a first plurality of heart tissue. Electrical data from the first plurality of heart tissue is recorded. The mapping assembly is repositioned such that at least one electrode from each spine contacts a second different plurality of heart tissue. Electrical data from the second plurality of heart tissue is then recorded.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
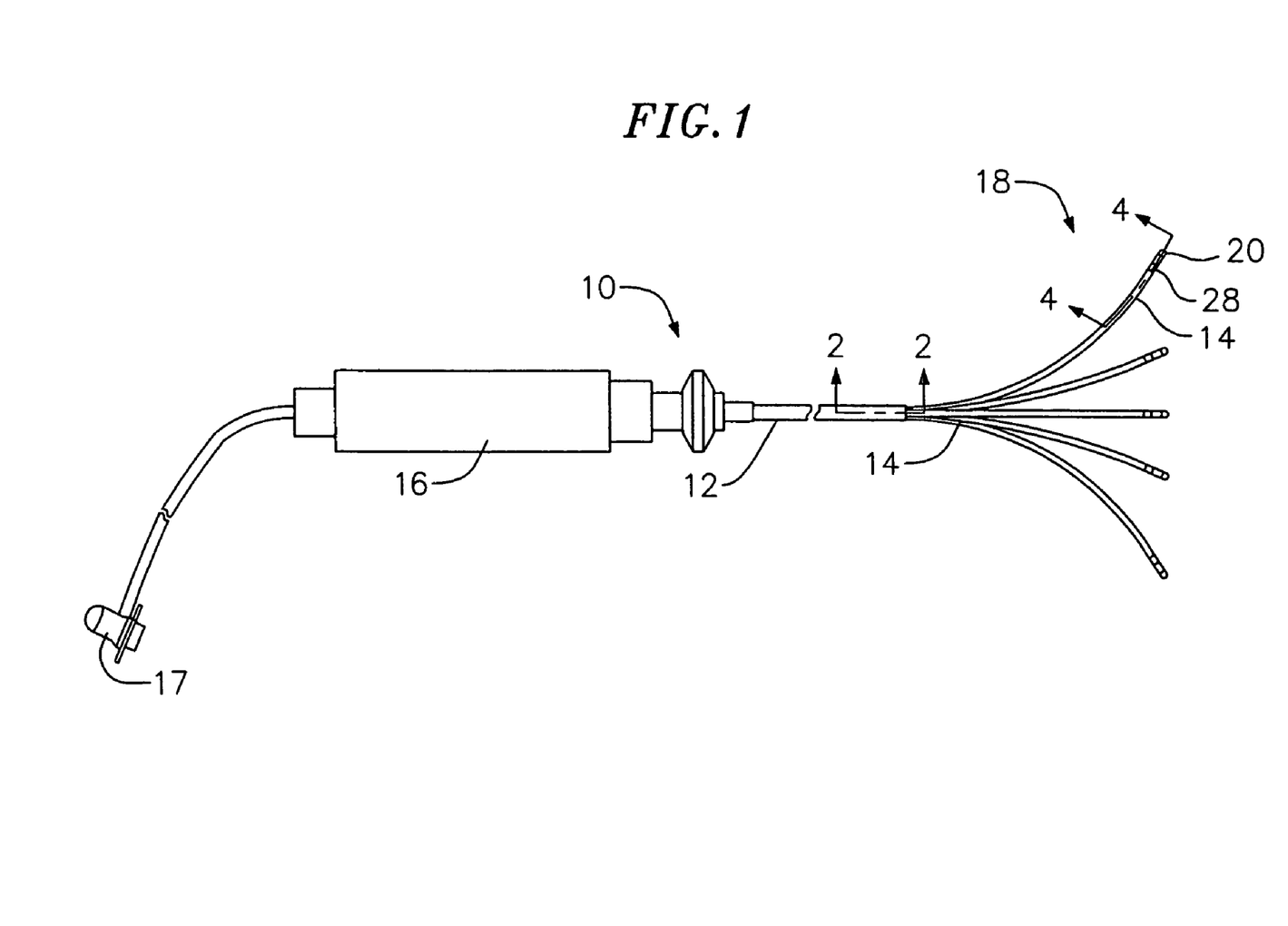
FIG. 1 is a perspective view of a catheter according to the invention.

The invention is directed to a catheter having a mapping assembly comprising a plurality of spines. Each spine carries at least one electrode, preferably a tip electrode and at least one ring electrode, such that when the spines are positioned in contact with heart tissue, each spine is capable of obtaining electrical, mechanical and locational data. As shown in FIG. 1, the catheter 10 comprises an elongated catheter body 12 having proximal and distal ends, a control handle 16 at the proximal end of the catheter body 12, and a mapping assembly 18 comprising a plurality of spines 14 mounted at the distal end of the catheter body 12.

Figure 2:
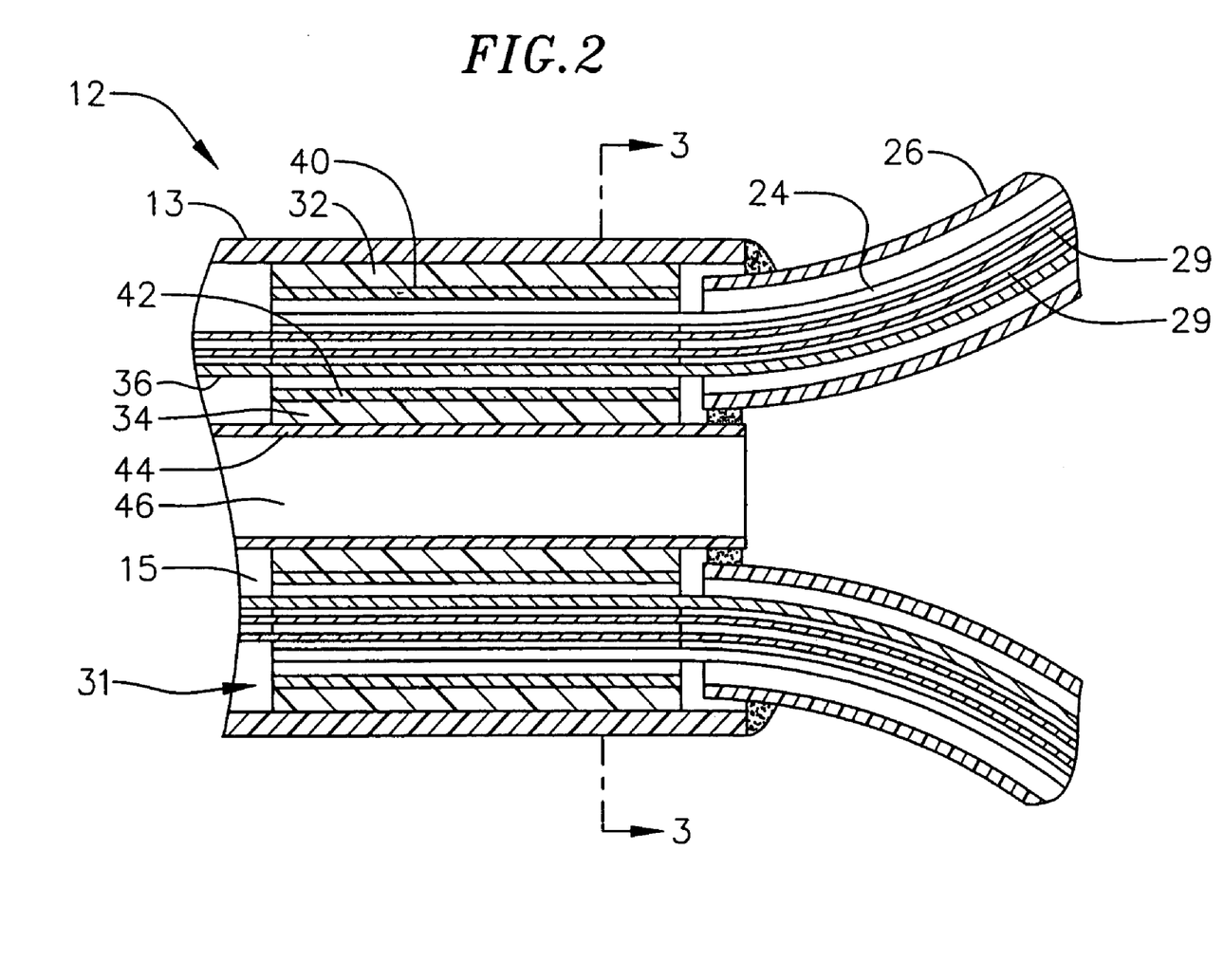
FIG. 2 is a side cross-sectional schematic view of a portion of the catheter of FIG. 1, taken from line 2—2 in FIG. 1.

As shown in FIGS. 1 and 2, the catheter body 12 comprises an elongated tubular construction having a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 13 made of polyurethane or PEBAX® (polyether block amide). The outer wall 13 comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 13 is not critical, but is preferably thin enough so that the central lumen 15 can accommodate lead wires, sensor cables and any other wires, cables or tubes. If desired, the inner surface of the outer wall 13 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In the depicted embodiment, the mapping assembly 18 comprises five spines 14. Each spine 14 has a proximal end attached at the distal end of the catheter body 12 and a free distal end, i.e., the distal end is not attached to any of the other spines, to the catheter body, or to any other structure that confines movement of the distal end. Each spine 14 contains a support arm 24 comprising a metal or plastic material that has shape memory, such that the support arm 24 forms an initial shape when no external forces are applied, forms a deflected shape when an external force is applied, and returns to its initial shape when the external force is released. In a preferred embodiment, the support arm 24 comprises a superelastic material, for example a nickel-titanium alloy, such as nitinol. Each spine 14 also comprises a non-conductive covering 26 in surrounding relation to the support arm 24. In a preferred embodiment, the non-conductive covering 26 comprises a biocompatible plastic tubing, such as a polyurethane or polyimide tubing.

As will be recognized by one skilled in the art, the number of spines 14 can vary as desired depending on the particular application, so that the catheter 10 has at least two spines, preferably at least three spines, more preferably at least five spines and as many as eight or more spines. As described in more detail below, the spines 14 are moveable between an expanded arrangement, wherein, for example, each spine extends radially outwardly from the catheter body 12, or the spines 14 may be arranged in a collapsed arrangement, wherein, for example, each spine is disposed generally along a longitudinal axis of the catheter body 12 so that the spines are capable of fitting within a lumen of a guiding sheath, as discussed further below.

Each spine 14 carries at least one electrode mounted along its length, preferably at or near its distal end. In the depicted embodiment, a tip electrode 20 is mounted on a distal end of each non-conductive covering 26 and at least one ring electrode 28 is mounted on each non-conductive covering 26, preferably on the distal end of the non-conductive covering 26. In this bipolar arrangement, the ring electrode 28 is used as a reference electrode. The distance between the tip electrode and ring electrode preferably ranges from about 0.5 mm to about 2 mm. In an alternative bipolar arrangement (not shown), the tip electrode 20 is eliminated and at least two ring electrodes 28 are mounted on each non-conductive covering 26, preferably on the distal end of the non-conductive covering 26. Another alternative embodiment (not shown), is a unipolar arrangement, in which the tip electrode 20 is mounted on the distal end of each non-conductive covering 26, with one or more reference ring electrodes mounted on the distal end of the catheter body 12, or one or more reference electrodes attached outside the body of the patient (e.g., in the form of a patch). In an alternative unipolar arrangement, a ring electrode 28 mounted on each non-conductive covering 26, preferably on the distal end of the non-conductive covering 26, is used instead of a tip electrode 20. Two, three or more ring electrodes 23 can be included as desired.

Each tip electrode 20 has an exposed length preferably ranging from about 0.5 mm to about 4 mm, more preferably from about 0.5 mm to about 2 mm, still more preferably about 1 mm. Each ring electrode 28 has a length preferably up to about 2 mm, more preferably from about 0.5 mm to about 1 mm.

Each tip electrode 20 and each ring electrode 28 is electrically connected to an electrode lead wire 29, which in turn is electrically connected to a connector 17. The connector 17 is connected to an appropriate mapping or monitoring system (not shown). Each electrode lead wire 29 extends from the connector 17, through the control handle 16, through the central lumen 15 in the catheter body 12, and into the non-conductive covering 26 of the spine 14 where it is attached to its corresponding tip electrode 20 or ring electrode 28. Each lead wire 29, which includes a non-conductive coating over almost all of its length, is attached to its corresponding tip electrode 20 or ring electrode 28 by any suitable method.

A preferred method for attaching a lead wire 29 to a ring electrode 28 involves first making a small hole through an outer wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the ring electrode 28, which is then slid into position over the hole and fixed in place with polyurethane glue or the like. Alternatively, each ring electrode 28 may be formed by wrapping the lead wire 29 around the non-conductive covering 26 a number of times and stripping the lead wire of its own non-conductive coating on its outwardly facing surfaces. In such an instance, the lead wire 29 functions as a ring electrode.

In the depicted embodiment, each spine 14 also includes at least one location sensor 30. The location sensor 30 is mounted near the distal end of each spine. In the depicted embodiment, where each spine 14 comprises a tip electrode 20, a location sensor 30 is mounted such that the distal end of the location sensor 30 is secured within its corresponding tip electrode 20, while the proximate end of the location sensor 30 extends into the distal end of the non-conductive covering 26. Each location sensor 30 is used to determine the coordinates of its corresponding tip electrode 20 at each instant when the tip electrode 20 is being used to collect an electrical mapping data point. As a result, both electrical and locational data can be obtained for each data point that is mapped. If the spine 14 carries at least one ring electrode 28 but does not include a tip electrode 20, the location sensor 30 is mounted near the distal end of the non-conductive covering 26, preferably as close to the distal end of the spine 14 as possible or in a plane concentric with the ring electrode 28.

Each location sensor 30 is connected to a corresponding sensor cable 36. Each sensor cable 36 extends through the non-conductive covering 26, catheter body 12 and control handle 16 and out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. Each sensor cable 36 comprises multiple wires encased within a plastic covered sheath. In the sensor control module, the wires of the sensor cable 36 are connected to the circuit board. The circuit board amplifies the signal received from the corresponding location sensor 30 and transmits it to a computer in a form understandable by the computer by means of a sensor connector at the proximal end of the sensor control module. Also, because the catheter 10 is designed for single use only, the circuit board preferably contains an EPROM chip that shuts down the circuit board approximately twenty-four hours after the catheter 10 has been used. This prevents the catheter 10, or at least the location sensors 30, from being used twice.

Preferably each location sensor 30 is an electromagnetic location sensor. For example, each location sensor 30 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 30 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. A particularly preferred location sensor 30 is a single axis sensor having a length ranging from about 3 mm to about 7 mm, preferably about 4 mm, such as that described in the U.S. patent application Ser. No. 09/882,125 filed Jun. 15, 2001, entitled "Position Sensor Having Core with High Permeability Material," the disclosure of which is incorporated herein by reference. Smaller sensors are particularly desirable for use in the present invention because of the need to keep the diameters of the spines 14 small enough so that they all fit within the lumen of a guiding sheath.

Figure 4:
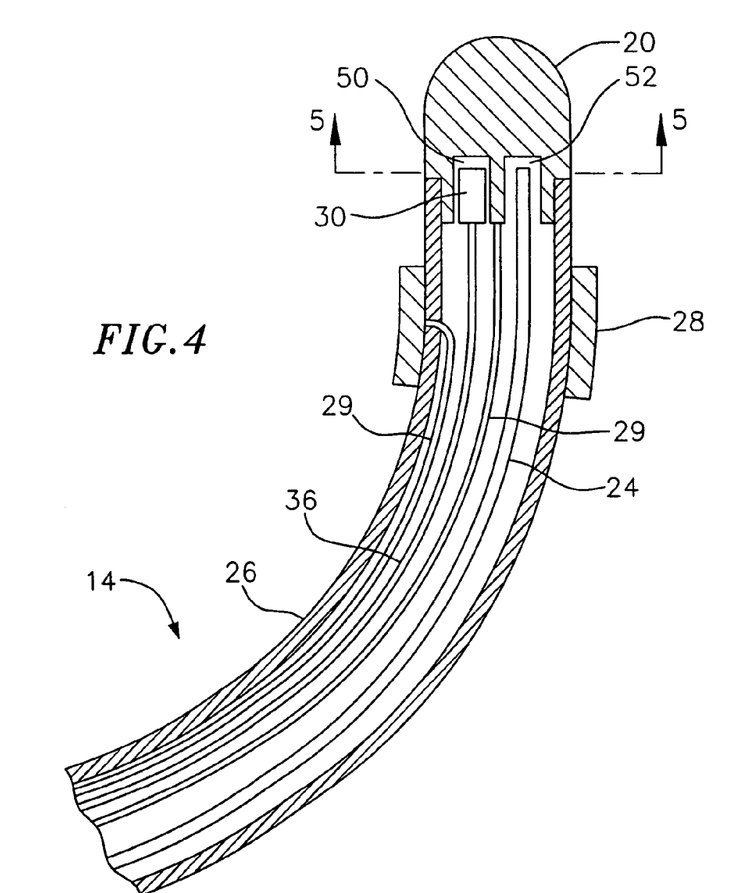
FIG. 4 is a side cross-sectional schematic view of one of the spines of the catheter of FIG. 1, taken from line 4—4 in FIG. 1.
Figure 5:
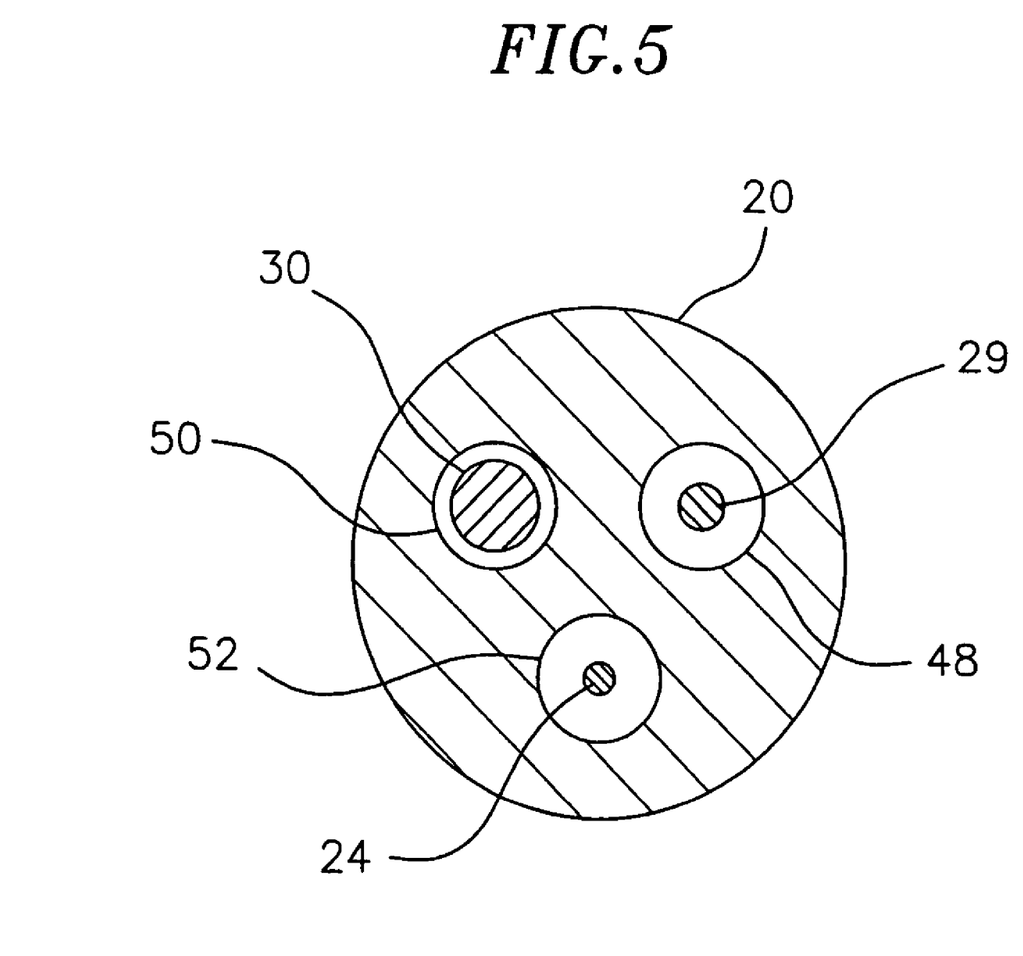
FIG. 5 is an end cross-sectional view of the tip electrode of the spine of FIG. 4, taken from line 5—5 in FIG. 4.

FIGS. 4 and 5 illustrate a suitable technique for mounting the electrode lead wire 29, the location sensor 30 and the support arm 24 to the tip electrode 20. The electrode lead wire 29 may be secured to the tip electrode 20 by drilling a first blind hole 48, preferably a bore hole, into the tip electrode 20, stripping the lead wire 29 of any coating and placing the lead wire 29 within the first blind hole 48 where it is electrically connected to the tip electrode 20 by a suitable means, such as by soldering or welding. The lead wire 29 may then be fixed in place, for example, by using a polyurethane glue or the like. The location sensor 30 may be similarly affixed to the tip electrode 20. For example, a second blind hole 50, preferably a bore hole, may be drilled into the tip electrode 20 such that the location sensor 30 may be inserted into the second blind hole 50 and affixed therein, for example, using a polyurethane glue or the like. The support arm 24 may also be similarly affixed to the tip electrode 20. For example, a third blind hole 52, preferably a bore hole, may be drilled into the tip electrode 20 such that the support arm 24 may be inserted into the third blind hole 52 and affixed therein, for example, using a polyurethane glue or the like.

Alternatively, a single blind hole (not shown) in the proximal end of the tip electrode 20 can be used for mounting the location sensor 30 and support arm 24, and the distal end of the lead wire 29 can be wrapped around the outside proximal end of the tip electrode, which is not exposed and attached by solder, welding or any other suitable technique. Any other arrangement for mounting these components in the spine could also be used.

Figure 3:
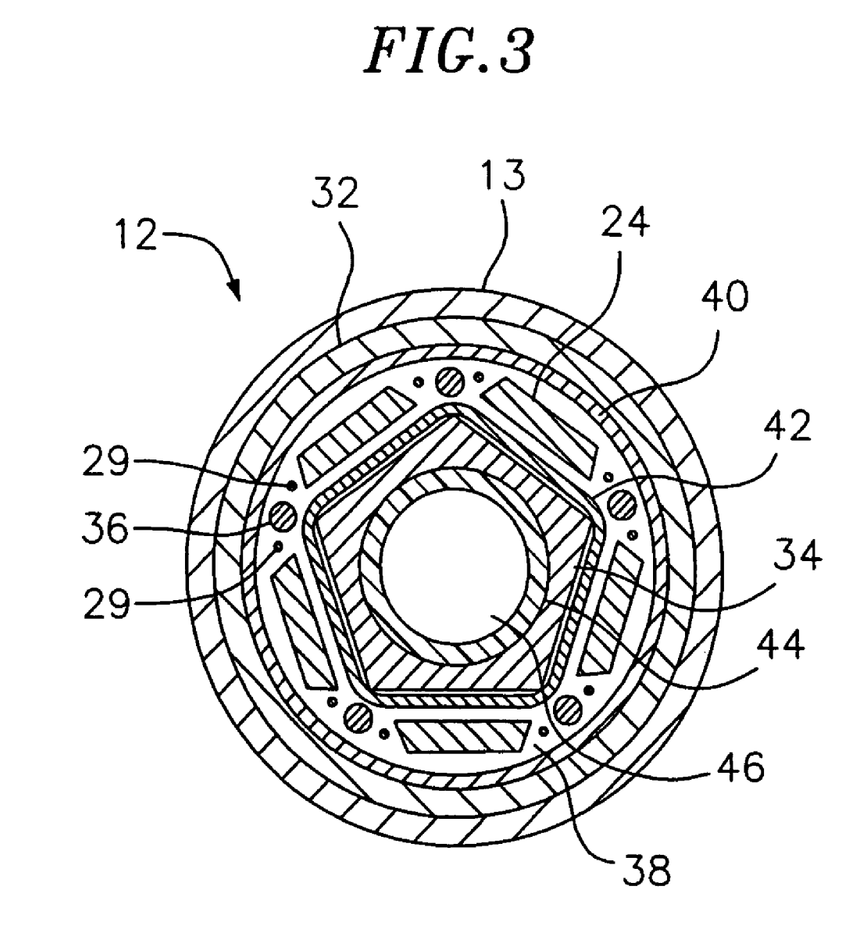
FIG. 3 is an end cross-sectional view of a portion of the catheter of FIG. 1, taken from line 3—3 in FIG. 2.

A suitable construction of the distal end of the catheter body 12, having spines 14 mounted thereto, is depicted in FIGS. 2 and 3. For clarity, only two spines 14 are shown in FIG. 2. Mounted in the distal end of the lumen 15 of the catheter body 12 is a spine mounting assembly 31. The spine mounting assembly 31 comprises an outer mounting ring 32 disposed within the outer wall 13 of the catheter body 12. The outer mounting ring 32 preferably comprises a metal material, such as stainless steel, more particularly stainless steel 303, and may be attached at the distal end of the catheter body 12 by a variety of methods, such as by welding or by use of an adhesive, such as a polyurethane glue. Alternatively, the outer mounting ring 32 may comprise a plastic material. A mounting structure 34 is provided coaxially within the outer mounting ring 32. In the depicted embodiment, the mounting structure 34 is multi-sided and comprises a metal material, such as stainless steel, more particularly stainless steel 303. The mounting structure 34 may also alternatively comprise a plastic material. The outer mounting ring 32 and the mounting structure 34 provide a channel 38 in which the proximal end of each support arm 24 is mounted. Specifically, each spine 14 is mounted in the catheter body 12 by removing a portion of the non-conductive covering 26 at the proximal end of each spine 14, inserting the distal end of each support arm 24 into the channel 38 between the outer mounting ring 32 and the multi-sided mounting structure 34 and affixing each support arm 24 within the channel 38 by any suitable means, such as with a polyurethane glue or the like. The lead wires 29 and sensor cables 36 also extend through the channel 38 between the outer mounting ring 32 and the mounting structure 34.

In a preferred embodiment, the support arm 24 has a generally trapezoidally-shaped end cross section with curved sides. In such an arrangement, when each support arm 24 is inserted into the channel 38, a substantially flat surface of each support arm 24, preferably the base of the trapezoidally-shaped end cross section, is mounted against a substantially flat surface on the multi-sided mounting structure 34. Preferably the number of substantially flat outer surfaces on the multi-sided mounting structure 34 corresponds to the number of spines 14. In such an instance, the support arm 24 of each spine 14 may be mounted within the channel 38 and adjacent to its corresponding side on the multi-sided mounting structure 34 to enable the support arms 24, and thus the spines 14, to be equally spaced around the multi-sided mounting structure 34. The multi-sided mounting structure 34 may be approximately co-axial with the longitudinal axis of the catheter body 12 such that the spines 14 are equally spaced about the catheter body 12 as well. Once each support arm 24 is properly positioned within the channel 38, each support arm 24 may be affixed within the channel 38 by any suitable means, such as by use of an adhesive, such as a polyurethane glue. Alternatively, the mounting structure 34 can have a round outer surface, although with such an embodiment more care needs to be taken if the support arms 24 are to be evenly spaced about the mounting structure.

In the depicted embodiment, a first non-conducting tube 40 is disposed between the outer mounting ring 32 and the support arms 24, and a second non-conducting tube 42 is disposed between the support arms 24 and the mounting structure 34. The non-conducting tubes 40 and 42, which may be polyimide tubes, ensure that each support arm 24 remains electrically isolated.

An irrigation tube 44 extends, preferably coaxially, through the mounting structure 34. The irrigation tube 44 preferably comprises a non-conductive material such as PEBAX, polyimide or polyurethane. The irrigation tube 44 extends through the catheter body 12 and out through the control handle 16 or out a sidearm (not shown) as is known in the art and described in U.S. Pat. No. 6,120,476, the disclosure of which is incorporated herein by reference. As discussed further below, the irrigation tube 44 is used to introduce irrigation fluid to the region between the spines, which is prone to thrombus formation resulting in adverse events and difficulties in removing the catheter from the patient. The distal end of the irrigation tube 44 is preferably glued in place between the spines 44. As would be recognized by one skilled in the art, the irrigation tube 44 can comprise a plurality of structures that define a continuous path through the catheter body 12 and into the handle 16, including a combination of one or more lumens and one or more tubes.

As previously discussed, when mounting the support arms 24 to the spine mounting assembly 31, a portion of the non-conductive covering 26 at the proximal end of each spine 14 is removed to expose the support arm 24. Removing a portion of the non-conductive covering 26 at the proximal end of each spine 14 enables the electrode lead wires 29 and sensor cables 36, corresponding to each tip electrode 20, ring electrode 28 and location sensor 30, to extend from the lumen 15 of the catheter 12, through the mounting ring lumen 46, and into each non-conductive covering 26. As shown in FIG. 4, once inserted into the non-conductive coverings 26, the electrode lead wires 29 and sensor cables 36 extend within the non-conductive covering 26 and are electrically connected at their distal ends to their corresponding tip electrode 20, ring electrode 28 or location sensor 30.

Figure 6:
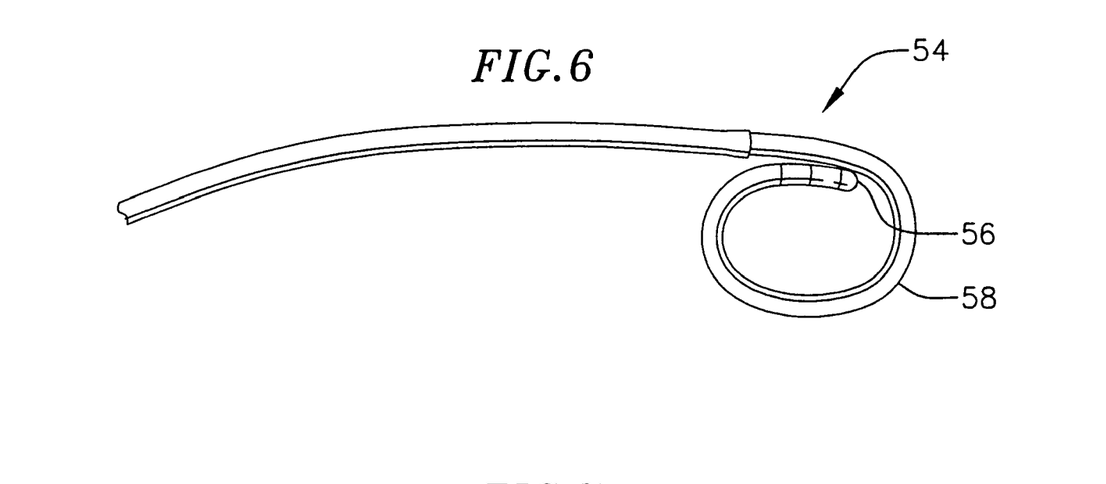
FIG. 6 is a perspective view of a pigtail dilator useful for introduction of the catheter of FIG. 1 into a patient.

To use the catheter 10 of the invention, a cardiologist or electrophysiologist introduces a guiding sheath and a dilator into the patient, as is generally known in the art, so that the distal ends of the sheath and dilator are in the region of the heart to be mapped. In some instances, such as when it is desired to insert the catheter 10 into the left ventricle through the aortic valve in a direction opposite the blood flow, it is preferable to use a pigtail-shaped dilator 54 having a distal end 56 that forms a loop 58, as shown in FIG. 6. Specifically, the side of the loop 58 is pushed against the flaps of the valve and serves essentially as a blunt instrument to push the flaps inward so that they are temporarily inverted while the dilator and guiding sheath are advanced through the valve. By using the surface of the loop 58 to push the flaps of the valve, potential puncturing of the flaps of the valve can be avoided. In contrast, pushing the flaps with a dilator having a straight distal end can potentially puncture or otherwise damage the flaps. After the dilator and guiding sheath having been advanced through the valve with the loop 58 inside the left ventricle, the flaps of the aortic valve return to their original, natural position.

Thereafter, the dilator is removed from the guiding sheath, and the catheter 10 is introduced into the patient through the guiding sheath. To insert the catheter 10 into the guiding sheath, the mapping assembly 18 must be in its collapsed arrangement, wherein each spine 14 is disposed generally along the longitudinal axis of the catheter body 12. A suitable guiding sheath for use in connection with the catheter 10 is the PREFACE™ Braided Guiding Sheath (commercially available from Biosense Webster, Inc., Diamond Bar, Calif.). Such a guiding sheath has sufficient strength to hold each support arm 24 in the collapsed arrangement, such that the spines 14 and also the entire remainder of the catheter 10 can travel within the guiding sheath, from an insertion point in the patient, through a vein or artery and to a desired location in the heart.

Once the distal end of the catheter has reached the desired location, such as a position within the left ventricle of the heart, relative longitudinal movement between the catheter 10 and the guiding sheath is provided to allow at least a portion of each spine 14 to protrude from the guiding sheath. Preferably the guiding sheath is moved proximally relative to the distal end of the catheter to expose the spines 14. When a portion of each spine 14 protrudes from the guiding sheath and a compression force is no longer applied by the guiding sheath on the spines, the shape memory of the support arms 24 allows the support arms to revert to a first expanded arrangement. In the first expanded arrangement, at least one electrode from each spine 14 can be placed into contact with a first plurality of the heart tissue such that electrical, locational and mechanical information can be obtained from the contacted heart tissue. The spines 14 can then be repositioned to a second expanded arrangement to contact a second plurality of heart tissue such that electrical, locational and mechanical information can be obtained from these tissues as well. This repositioning is preferably achieved by further moving the guiding sheath proximally relative to the catheter to thereby expose a greater portion of each spine. In the depicted embodiment, the more of each spine that is exposed, the further each spine can bend or expand away from the catheter to thereby contact heart tissue. This process can be repeated until the heart has been satisfactorily mapped.

After mapping is completed, the catheter is moved proximally relative to the guiding sheath to retract the spines within the sheath. During mapping, the region between the spines 14 can be prone to thrombus formation, which can make it difficult to withdraw the spines back into the sheath. To minimize such thrombus formation, irrigation fluid is introduced through the irrigation tube 44 before, during and/or after a mapping procedure to flush the region between the spines 14. Preferably irrigation is provided continuously during the procedure to minimize any potential blood clotting in the irrigation tube. Suitable irrigation fluids for use in connection with the invention include saline, heparinized saline and thrombolitica. Although the irrigation tube 44 is preferably positioned coaxial with the catheter body 12 so that it is mounted between all of the spines, other positions for the irrigation tube at or near the distal end of the catheter can be used in accordance with the present invention.

Figure 7:
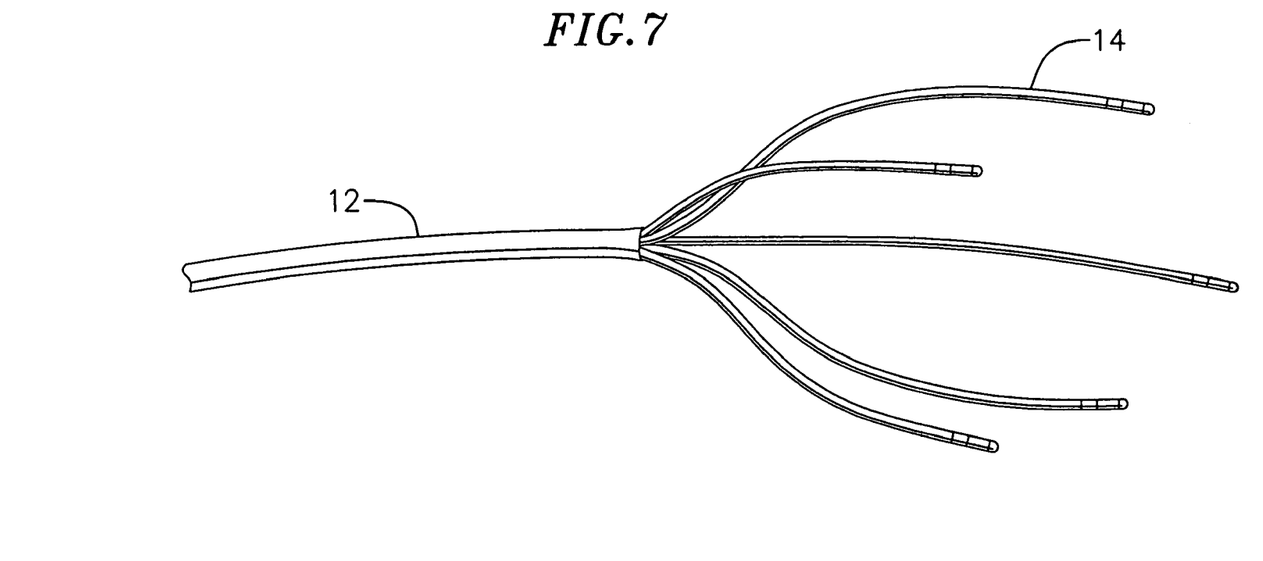
FIG. 7 is a perspective view of an alternative embodiment of an expanded arrangement of the mapping assembly of a catheter according to the invention.
Figure 8:
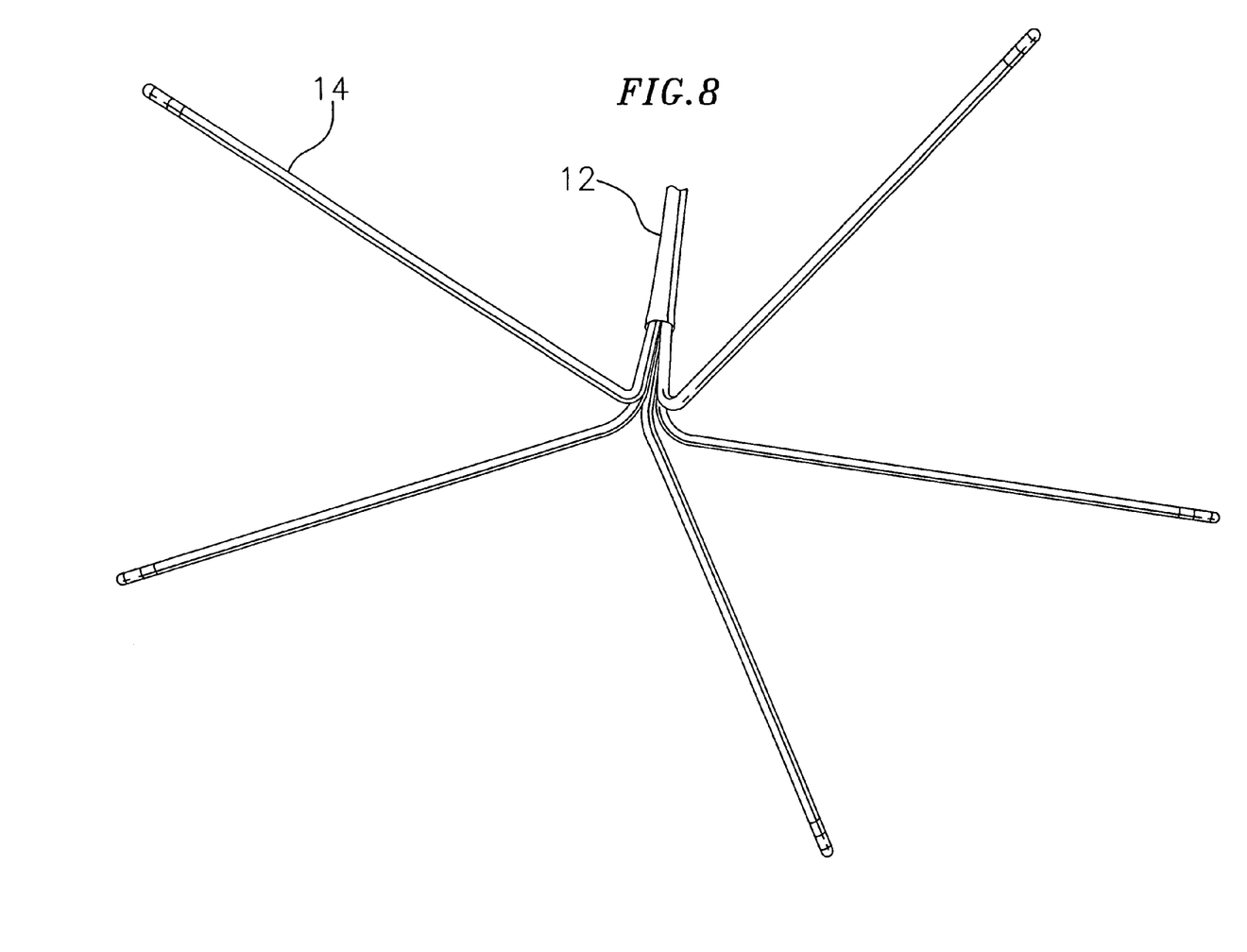
FIG. 8 is a perspective view of another alternative embodiment of an expanded arrangement of the mapping assembly of a catheter according to the invention.

The expanded arrangement of spines 14 can take on various shapes. For instance, in the above-described embodiment, each spine 14 extends radially outwardly from the catheter body 12 and forms an outwardly curved shape as shown in FIG. 1. In another embodiment, shown in FIG. 8, each spine 14 extends radially outwardly from the catheter body 12 and forms a substantially straight line, which is preferably substantially perpendicular to the catheter body 12. In still another embodiment, shown in FIG. 7, each spine 14 bows radially outwardly such that the spines 14, taken together, form a cup shape.

Using the inventive catheter 10 having multiple spines 14, each having electrical and mechanical mapping and locational sensing capabilities, the cardiologist can map local activation time and obtain voltage maps. The cardiologist can also determine those locations in the heart having no mechanical activity by monitoring whether the position of the location sensor changes over a complete cardiac cycle. This information can guide the cardiologist in providing therapy to the patient. For example, where the cardiologist finds regions of the heart that do not have mechanical activity, he or she can revascularize those regions using known techniques, such as gene therapy or transmyocardial revasularization. The inventive catheter 10 allows the cardiologist to map the heart more quickly than traditional catheters by measuring multiple points of data at a time.

If desired, the catheter may include a steering mechanism for deflection of the distal end of the catheter body 12. With such a design, the distal end of the catheter body 12 preferably comprises a short length of tubing, e.g., 2 to 4 inches in length, that is more flexible than the remainder of the catheter body 12. A suitable steering mechanism comprises a puller wire (not shown) that extends from a proximal end in the control handle 16, through the central lumen 15 in the catheter body 12 and into an off axis lumen in the short length of tubing. Within the catheter body 12, the puller wire extends through a closely wound coil that is bendable but substantially non-compressible. The coil is fixed near the proximal and distal ends of the catheter body 12 and prevents deflection of the catheter body 12. The distal end of the puller wire is anchored at the distal end of the short length of tubing in the off axis lumen. The proximal end of the puller wire is anchored to a movable member in the handle 16 that can be moved relative to the catheter body 12. Proximal movement of the movable member relative to the catheter body 12 results in deflection of the short length of tubing. An example of such a steering mechanism and construction is described in more detail in U.S. Pat. No. 6,064,905, the disclosure of which is incorporated herein by reference. When incorporating a steering mechanism into the inventive catheter 10, it may be desirable to include a location sensor at the distal end of the catheter body 12. As would be recognized by one skilled in the art, of a slurring mechanism is not including, the handle 16 can be eliminated, although it is described to maintain the handle for ease of use by the cardiologist.

The preceding description has been presented with references to presently preferred embodiments of the invention. Persons skilled in the art and technology to which this invention pertains will appreciate that alterations and changes in the described structures can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

What is claimed is:

1. A method for mapping Purkinje fibers in a region of the heart comprising:
   introducing into the region of the heart to be mapped the distal end of a catheter comprising:
      an elongated catheter body having a proximal end, a distal end and at least one lumen extending longitudinally therethrough,
      a mapping assembly mounted at the distal end of the catheter body and comprising at least two spines, each spine having a proximal end attached at the distal end of the catheter body and a free distal end, wherein each spine comprises at least one electrode; and
      an irrigation tube extending through the catheter body and having an open distal end that is in communication with the outside of the distal end of the catheter body, the irrigation tube having a distal end terminating at the distal end of the catheter body, the irrigation tube being adapted to deliver irrigation fluid to a region between the spines of the mapping assembly;
   positioning the mapping assembly so that at least one electrode from each spine is in contact with a first plurality of heart tissue;
   recording electrical data from the first plurality of heart tissue;
   repositioning the mapping assembly such that at least one electrode from each spine contacts a second different plurality of heart tissue; and
   recording electrical data from the second plurality of heart tissue.

2. The method of claim 1, wherein the distal end of the catheter is introduced through a guiding sheath having a distal end positioned in the heart so that the spines of the mapping assembly are covered by the guiding sheath.

3. The method of claim 2, wherein the positioning and repositioning steps comprise moving the guiding sheath proximally relative to the mapping assembly.

4. The method of claim 1, wherein each spine comprises a tip electrode mounted at or near the distal end of the spine.

5. The method of claim 1, wherein each spine further comprises at least one location sensor.

6. The method of claim 1, wherein each spine comprises a non-conductive covering having a support arm that has shape memory disposed therein.

7. A method for mapping Purkinje fibers in a region of the heart comprising:
   introducing into the region of the heart to be mapped the distal end of a catheter comprising:
      an elongated catheter body having a proximal end, a distal end and at least one lumen extending longitudinally therethrough,
      a mapping assembly mounted at the distal end of the catheter body and comprising at least two spines, each spine having a proximal end attached at the distal end of the catheter body and a free distal end, wherein each spine comprises a tip electrode and at least one ring electrode, each spine further comprising at least one location sensor; and
      an irrigation tube extending through the catheter body and having an open distal end that is in communication with the outside of the distal end of the catheter body;
   positioning the mapping assembly so that at least one electrode from each spine is in contact with a first plurality of heart tissue;
   recording electrical data from the first plurality of heart tissue;
   repositioning the mapping assembly such that at least one electrode from each spine contacts a second different plurality of heart tissue; and
   recording electrical data from the second plurality of heart tissue.

* * * * *